US00PP17072P2

(12) United States Plant Patent
Jonkers

(10) Patent No.: US PP17,072 P2
(45) Date of Patent: Aug. 29, 2006

(54) ***IMPATIENS* PLANT NAMED 'BUTLY CHER'**

(50) Latin Name: ***Impatiens walleriana*×*Impatiens pseudoviola***
Varietal Denomination: Butly Cher

(75) Inventor: Johanna B. Jonkers, Andijk (NL)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 11/210,222

(22) Filed: Aug. 23, 2005

(51) Int. Cl.
*A01H 5/00* (2006.01)

(52) U.S. Cl. ..... Plt./317

(58) Field of Classification Search ..... Plt./317
See application file for complete search history.

*Primary Examiner*—Kent Bell
(74) *Attorney, Agent, or Firm*—Jondle & Associates, P.C.

(57) ABSTRACT

An *Impatiens* cultivar particularly distinguished by large red-purple flowers, large foliage and a large plant size, good vigor and a trailing habit is disclosed.

1 Drawing Sheet

Genus and species: *Impatiens walleriana*×*Impatiens pseudoviola.*
Variety denomination: 'Butly Cher'.

BACKGROUND OF THE NEW PLANT

The present invention comprises a new and distinct cultivar of *impatiens*, botanically known as *Impatiens walleriana*×*Impatiens pseudoviola,* and hereinafter referred to by the cultivar name 'Butly Cher'. The new cultivar originated from a hybridization made in the year 2002 in Andijk, The Netherlands. The female parent was 'IMO-18-2' a red proprietary line (unpatented), while the male parent was 'SPZ-1-21', a lavender proprietary line (unpatented).

The new cultivar was created in 2002 in Andijk, The Netherlands and has been asexually reproduced repeatedly by vegetative cuttings and tissue culture in Gilroy, Calif. and Andijk, The Netherlands over a three-year period. The plant has also been trialed at Gilroy, Calif., Litchfield, Mich. and Andijk, The Netherlands. The present invention has been found to retain its distinctive characteristics through successive asexual propagations.

SUMMARY OF THE INVENTION

The following are the most outstanding and distinguishing characteristics of this new cultivar when grown under normal horticultural practices in Gilroy, Calif. and Andijk, The Netherlands.

1. Large red-purple flowers;
2. Large foliage and plant size; and
3. Good vigor and a trailing habit.

DESCRIPTION OF PHOTOGRAPH

This new *impatiens* plant is illustrated by the accompanying photograph which shows overall plant habit including blooms, buds, and foliage of the plant; the colors shown are as true as can be reasonably obtained by conventional photographic procedures. The photograph is of three 4½-month-old plants grown in an eight-inch pot in Andijk, The Netherlands in a greenhouse in a winter/spring trial setting.

The accompanying photograph shows overall plant habit including blooms, buds and foliage; the inset shows mature inflorescences.

DESCRIPTION OF THE NEW CULTIVAR

The following detailed descriptions set forth the distinctive characteristics of 'Butly Cher'. The data which defines these characteristics were collected from asexual reproductions carried out in Gilroy, Calif. The plant history was taken on 12-week-old plants grown in 6-inch pots in a poly-covered greenhouse in the early summer season. Color readings were taken under natural light in the greenhouse. Color references are primarily to The R.H.S. Colour Chart of The Royal Horticultural Society of London (R.H.S.) (2001). Texture description details were observed under a dissecting microscope.

DETAILED BOTANICAL DESCRIPTION

Classification:
- *Botanical.*—*Impatiens walleriana*×*Impatiens pseudoviola.*
- *Common name.*—*Impatiens.*

Parentage:
- *Female parent.*—'IMO-18-2' proprietary line (unpatented).
- *Male parent.*—'SPZ-1-21' proprietary line (unpatented).

Growth:
- *Form.*—Slightly upright and semi-trailing.
- *Growth and branching habit.*—Good basal branching; vigorous; pinching of the terminal apices enhances branching and floriferousness.
- *Height (from soil level to top of blooms).*—15–20 cm.
- *Width (including flowers).*—20–25 cm.
- *Time to produce a finished flowering plant.*—8–10 weeks for a 4-inch pot.
- *Outdoor plant performance.*—Does well in afternoon shade, free flowering in the spring, summer and fall; use in hanging baskets, mixed containers and window boxes.

*Time to initiate and develop roots.*—10–21 days.
*Root description.*—Fibrous, fleshy, and white.

Leaves:
*Arrangement.*—Alternate, whorls.
*Length.*—3.6–3.9 cm.
*Width.*—2.5–2.9 cm.
*Shape.*—Broadly ovate.
*Margin.*—Crenate, with one ciliate at each lobe.
*Apex.*—Acute.
*Base.*—Attenuate.
*Color.*—Upper surface: Closest to RHS 147A. Lower surface: RHS 147B.
*Texture.*—Glabrous.
*Venation.*—Pinnate.
*Venation color.*—RHS 144A.
*Petiole.*—Length: 1.8–2.0 cm. Diameter: 0.2 cm. Color: RHS 144A. Texture: Glabrous.

Stems:
*Length.*—8.0–15.0 cm.
*Diameter.*—0.4 cm.
*Internode length.*—1.0–1.5 cm.
*Color.*—RHS 144A.
*Texture.*—Glabrous.
*Stem anthocyanin.*—Present in small irregular blotches, reddish brown.
*Pedicel.*—Length: 3.5–3.7 cm. Diameter: 0.15–0.2 cm. Color: RHS 144C. Texture: Glabrous.
*Peduncle.*—Length: 4.0–4.1 cm. Diameter: 0.2 cm. Color: RHS 144A. Texture: Glabrous.

Flower buds:
*Shape.*—Ovate.
*Diameter:*—0.6–0.8 cm.
*Length:*—0.7–0.9 cm.
*Color at tight bud:—RHS* 63A.

Inflorescence:
*Blooming habit.*—Continuous and freely all through the spring, summer and fall.
*Inflorescence type.*—Racemes in leaf axis and in leaf whorls.
*Number of flowers per raceme and/or whorl.*—Approximately 10–20, including buds.
*Number of flowers per plant.*—Approximately 100–150.
*Lastingness of individual blooms on the plant.*—4–8 days.
*Fragrance.*—None.

Flowers:
*Floret form.*—5 petals, 1 standard or dorsal (free); 2 lateral or lobed pairs (wing petals), deeply lobed.
*Floret diameter.*—2.8–3.1 cm.
*Floret height.*—2.7–2.9 cm.
*Color, immature flowers, upper surface.*—Dorsal petal: RHS 60A. Lateral petals: RHS 60A.
*Color, immature flowers, lower surface.*—Dorsal petals: RHS 50C with RHS 50B margins. Lateral petals: RHS 50C with RHS 50B margins.
*Color, mature flowers, upper surface.*—Dorsal petal: RHS 60B. Lateral petal: RHS 60B, but redder.
*Color, mature flowers, lower surface.*—Dorsal petal: RHS 50C with RHS 50B at the margin. Lateral petal: RHS 50B with RHS 50A at the margin.

Petals:
*Quantity.*—5.
*Dorsal.*—Length: 1.5–1.6 cm. Width: 1.7–1.8 cm. Shape: Orbicular. Apex: Emarginate. Base: Fused. Margin: Entire. Texture: Papillose.
*Lateral.*—Length: 1.4–1.5 cm. Width: 0.8–0.9 cm. Shape: Spathulate. Apex: Praemorse. Base: Fused. Margin: Entire. Texture: Papillose.

Sepals:
*Quantity.*—3, 1 larger than the others, with a spur.
*Large sepal.*—Color: RHS 143B; RHS 143A keel. Length: 1.3–1.4 cm. Width: 1.1–1.2 cm. Shape: Broadly elliptical. Apex: Acute. Base: Fused. Texture: Glabrous. Spur: Color: A light hue of RHS 51D. Length: 2.2–2.4 cm.
*Small sepal.*—Color: RHS 143B. Length: 0.2 cm. Width: 0.1 cm. Shape: Ovate. Apex: Acute. Base: Fused. Texture: Glabrous.

Reproductive organs:
*Stamens.*—5; more or less fused by the anthers and covering the ovary.
*Pollen cap color.*—RHS 60C.
*Pollen amount.*—Not observed.
*Pistil.*—1, complete.

Fruit and seed set: Has not been observed.
Disease and insect resistance: Has not been observed.

COMPARISON WITH KNOWN CULTIVARS

'Butly Cher' differs from the female parent, 'IMO-18-2' proprietary line (unpatented), in that 'Butly Cher' has more vigor, is more branched, has a more pendulous habit and has larger flowers than 'IMO-18-2'. 'Butly Cher' differs from the male parent, 'SPZ-1-21' proprietary line (unpatented), in that 'Butly Cher' is more floriferous and has larger flowers than 'SPZ-1-21'.

'Butly Cher' differs from the commercial cultivar 'Fify Red' (U.S. Plant Pat. No. 11,753) in that 'Butly Cher' has a more open-petaled, red-purple flower, has a larger plant size with larger foliage, and has a more trailing habit than 'Fify Red'.

I claim:

1. A new and distinct cultivar of *Impatiens* plant as shown and described herein.

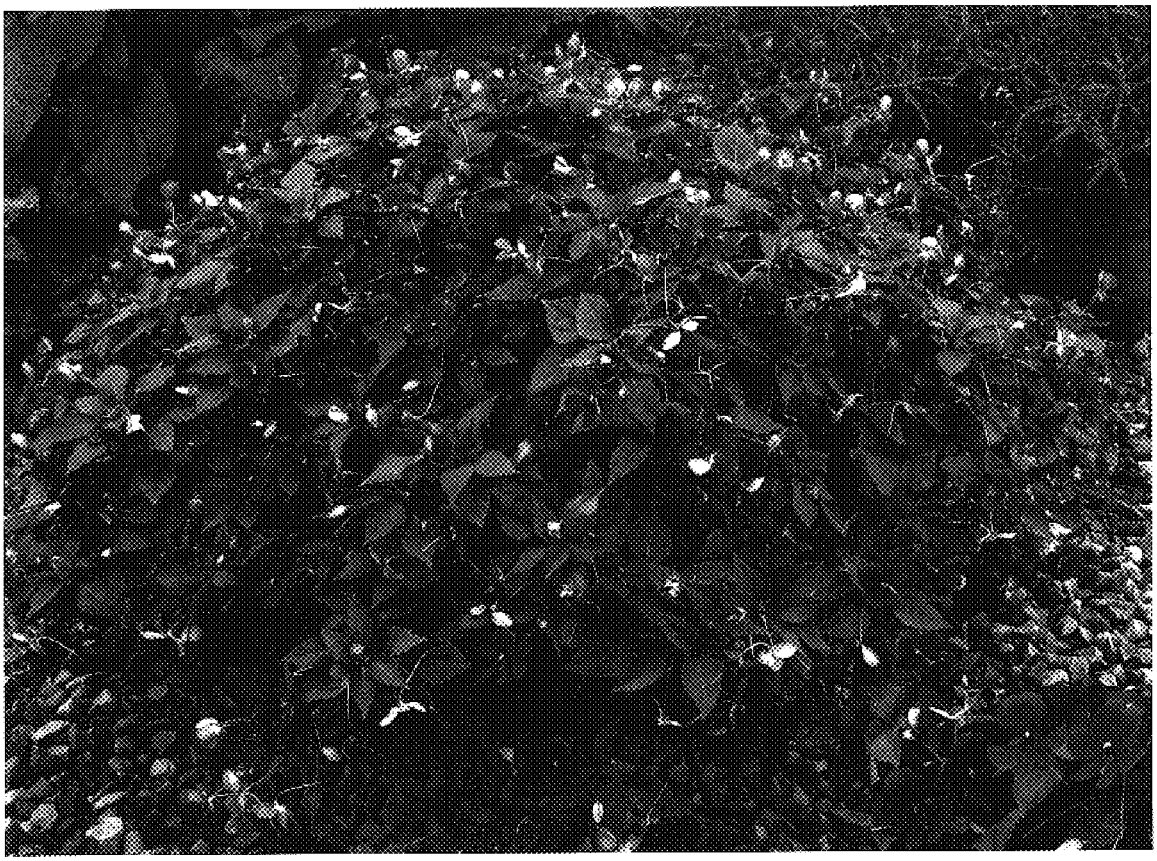

* * * * *